United States Patent [19]

Bills et al.

[11] Patent Number: 5,411,985
[45] Date of Patent: May 2, 1995

[54] GAMMA-PYRONE-3-ACETIC ACID AS AN INHIBITOR OR INTERLEUKIN-1 β INVENTORY ENZYME

[75] Inventors: Gerald F. Bills, Cranford; Otto D. Hensens, Red Bank; Jerrold M. Liesch, Princeton Junction; Russel B. Lingham, Watchung; Jon D. Polishook, Scotch Plains; Michael J. Salvatore, South Plainfield; Susan L. Raghoobar, Fords, all of N.J.

[73] Assignee: Merck & Co., Inc., Rahway, N.J.

[21] Appl. No.: 62,881

[22] Filed: May 17, 1993

[51] Int. Cl.$^6$ .............................................. A61K 31/35
[52] U.S. Cl. ..................................... 514/460; 549/420
[58] Field of Search ......................... 514/460; 549/420

[56] References Cited

U.S. PATENT DOCUMENTS 4,603,144  7/1986  Campbell et al. ................... 549/420

OTHER PUBLICATIONS

Engel, et al., Helv. Chim. Acta 32 pp. 1752–1758 (1949).
Mycofaxon (46) pp. 141–154 (1993) A Synoptic Key to Xylaria Species from Continental United States and Canada Based on Cultural and Anamorphic Features.

Primary Examiner—Richard L. Raymond
Attorney, Agent, or Firm—Curtis C. Panzer; David L. Rose

[57] ABSTRACT

Novel peptidyl derivatives of formula I are found to be potent inhibitors of interleukin-1β converting enzyme (ICE). Compounds of formula I may be useful in the treatment of inflammatory or immune-based diseases of the lung and airways; central nervous system and surrounding membranes; the eyes and ears; joints, bones, and connective tissues; cardiovascular system including the pericardium; the gastrointestinal and urogenital systems; the skin and mucosal membranes. Compounds of formula I are also useful in treating the complications of infection (e.g., gram negative shock) and tumors in which IL 1 functions as an autocrine growth factor or as a mediator of cachexia.

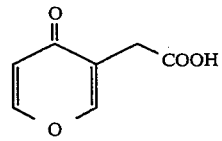

4 Claims, No Drawings

GAMMA-PYRONE-3-ACETIC ACID AS AN INHIBITOR OR INTERLEUKIN-1 β INVENTORY ENZYME

BACKGROUND OF THE INVENTION

This invention relates to gamma-pyrone-3-acetic acid and a process of making this compound. Applicants have found that gamma-pyrone-3-acetic acid is useful in the treatment of inflammation in lung, central nervous system, kidney, joints, endocardium, pericardium, eyes, ears, skin, gastrointestinal tract and urogenital system. Interleukin-1β converting enzyme (ICE) has been identified as the enzyme responsible for converting precursor interleukin-1β (IL- 1β) to biologically active IL-1β.

Mammalian interleukin-1 (IL-1) is an immunoregulatory protein secreted by cell types as part of the inflammatory response. The primary cell type responsible for IL-1 production is the peripheral blood monocyte. Other cell types have also been described as releasing or containing IL-1 or IL-1 like molecules. These include epithelial cells (Luger, et al., J. Immunol. 127:1493-1498 (1981), Le et al., J. Immunol. 138:2520-2526 (1987) and Lovett and Larsen, J. Clin. Invest. 82:115-122 (1988), connective tissue cells (Ollivierre et al., Biochem. Biophys. Res. Comm. 14 1: 904-911 (1986), Le et al, J. Immunol. 138:2520-2526 (1987), cells of neuronal origin (Giulian et al., J. Esp. Med. 164:594-604 (1986) and leukocytes (Pistoia et al., J. Immunol. 136:1688-1692 (1986), Acres et al., Mol. Immuno. 24:479-485 (1987), Acres et al., J. Immunol. 138: 2132-2136 (1987) and Lindenmann et al., J. Immunol 140:837-839 (1988).

Biologically active IL-1 exists in two distinct forms, IL-1α with an isoelectric point of about pI 5.2 and IL-1β with an isoelectric point of about 7.0 with both forms having a molecular mass of about 17,500 (Bayne et al., J. Esp. Med. 163:1267-1280 (1986) and Schmidt, J. Esp. Med. 160:772 (1984). The polypeptides appear evolutionarily conserved, showing about 27-33% homology at the amino acid level (Clark et al., Nucleic Acids Res. 14:7897-7914 (1986).

Mammalian IL-1β is synthesized as a cell associated precursor polypeptide with a molecular mass of about 31.4 kDa (Limjuco et al., Proc. Natl. Acad. Sci USA 83:3972-3976 (1986). Precursor IL-1β is unable to bind to IL-1 receptors and is biologically inactive (Mosley et al., J. Biol. Chem. 262:2941-2944 (1987). Biological activity appears dependent upon some form of proteolytic processing which results in the conversion of the precursor 31.5 kDa form to the mature 17.5 kDa form. Evidence is growing that by inhibiting the conversion of precursor IL-1β to mature IL-1β, one can effectively inhibit the activity of interleukin-1.

Mammalian cells capable of producing IL-1β include, but are not limited to, karatinocytes, endothelial cells, mesangial cells, thymic epithelial cells, derreal fibroblasts, chondrocytes, astrocytes, glioma cells, mononuclear phagocytes, granulocytes, T and B lymphocytes and NK cells.

As discussed by J. J. Oppenheim, et al. Immunology Today, vol. 7(2):45-56 (1986), the activities of interleukin-1 are many. It has been observed that Catabolin, a factor that promotes degradation of cartilage matrix, also exhibited the thymocyte comitogenic activities of IL-1 and stimulates chondrocytes to release collagenase neutral proteases and plasminogen activator. In addition, a plasma factor termed proteolysis inducing factor stimulates muscle cells to produce prostaglandins which in turn leads to proteolysis, the release of amino acids and, in the long run, muscle wasting, and appears to represent a fragment of IL-1 with fever-inducing, acute phase response and thymocyte co-mitogenic activities.

IL-1 has multiple effects on cells involved in inflammation and wound healing. Subcutaneous injection of IL-1 leads to margination of neutrophils and maximal extravascular infiltration of the polymorphonuclear leukocytes (PMN). In vitro studies reveal IL-1 to be a chemotactic attractant for PMN to activate PMN to metabolize glucose more rapidly to reduce nitroblue tetrazolium and to release their lysozomal enzymes. Endothelial cells are stimulated to proliferate by IL-1 to produce thromboxane, to become more adhesive and to release procoagulant activity. IL-1 also enhances collagen type IV production by epidermal cells, induces osteoblast proliferation and alkaline phosphatase production and stimulates osteoclasts to resorb bone. Even macrophages have been reported to be chemotactically attracted to IL-1 to produce prostaglandins in response to IL-1 and to exhibit a more prolonged and active tumoricidal state.

IL-1 is also a potent bone resorptive agent capable upon infusion into mice of causing hypercaleemia and increase in bone resorptive surface as revealed by his to morphometry Sabatini, M. et al., PNAS 85: 5235-5239, 1988.

Accordingly, disease states in which the ICE inhibitors of Formula I may be useful as therapeutic agents include, but are not limited to, infectious diseases where active infection exists at any body site, such as meningitis and salpingitis; complications of infections including septic shock, disseminated intravascular coagulation, and/or adult respiratory distress syndrome; acute or chronic inflammation due to antigen, antibody, and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis. Immune-based diseases which may be responsive to ICE inhibitors of Formula I include but are not limited to conditions involving T-cells and/or macrophages such as acute and delayed hypersensitivity, graft rejection, and graft-versus-host-disease; auto-immune diseases including Type I diabetes mellitus and multiple sclerosis. ICE inhibitors of Formula I may also be useful in the treatment of bone and cartilage resorption as well as diseases resulting in excessive deposition of extracellular matrix. Such diseases include peridonate diseases interstitial pulmonary fibrosis, cirrhosis, systemic sclerosis, and keloid formation. ICE inhibitors of Formula I may also be useful in treatment of certain tumors which produce IL 1 as an autocrine growth factor and in preventing the cachexia associated with certain tumors.

SUMMARY OF THE INVENTION

The invention is directed to gamma-pyrone-3-acetic acid, which has been found to be potent inhibitor of interleukin-1β converting enzyme (ICE). The invention is also directed to a process for making gamma-pyrone-3-acetic acid by the fermentation of the fungus MF5809, Xylaria sp.ATCC accession No. 74223, by submerged aerobic culture of a suitable aqueous medium, containing assimilable sources of carbon, nitrogen and inorganic salts.

DETAILED DESCRIPTION OF THE INVENTION

In one embodiment the invention encompasses compound I, gamma-pyrone-3-acetic acid

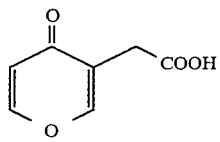   I which has been found to be potent inhibitor of interleukin-1β converting enzyme (ICE).

In a second embodiment the invention is directed to pharmaceutical compositions for inhibiting ICE and for treating ICE mediated diseases as disclosed herein comprising a non-toxic therapeutically effective amount of gamma-pyrone-3-acetic acid and a pharmaceutically acceptable carrier.

In a third embodiment the invention is directed to methods of inhibiting ICE and methods of treating ICE mediated diseases comprising: administration to a patient in need of such inhibition or treatment of a non-toxic therapeutically effective amount of gamma-pyrone-3-acetic acid.

Illustrative of these aspects, this invention concerns pharmaceutical compositions and methods of treatment of diseases selected from septic shock, allograft rejection, inflammatory bowel disease and rheumatoid arthritis in a patient in need of such treatment.

In a fourth embodiment the invention is directed to a process for making gamma-pyrone-3-acetic acid by the fermentation of the fungus MF5809, Xylaria sp. (AscomyCotina, Xylariales), ATCC accession No. 74223, by submerged aerobic culture of a suitable aqueous medium, containing assimilable sources of carbon, nitrogen and inorganic salts.

Within this embodiment the invention concerns a process for the preparation of gamma-pyrone-3-acetic acid which comprises:

(a) culturing a microorganism MF5809, Xylaria sp., ATCC accession No. 74223, or a mutant thereof, in a nutrient medium containing assimilable sources of nitrogen and carbon under aerobic conditions until a substantial amount of the compound is produced, and (b) isolating the compound so produced.

In a fifth embodiment the invention is directed to the present invention involves a biologically pure culture of MF5809, Xylaria sp., ATCC accession No. 74223, or a mutant thereof, capable of producing compound gamma-pyrone-3-acetic acid.

The culture was deposited under the Budapest Treaty with the American Type Culture Collection, Rockville, Md., on Apr. 15, 1993 under ATCC accession No. 74223 and is currently maintained as a biologically pure culture in the Merck Culture Collection as MF5809.

As indicated above, the present invention is not limited to a single strain of microorganism. Included within the scope of this invention is the use of other natural or artificial mutants or variants derived from the described culture. The artificial production of mutant strains of MF5809, Xylaria sp., ATCC accession No. 74223, may be achieved by physical or chemical mutagens, for example, ultraviolet irradiation or N-nitrosoguanidine treatment and the like. Recombinant. DNA techniques such as protoplast fusion, plasmid incorporation, gene transfer and the like are also envisioned.

The producing organism, MF5809, was isolated from living bark of a live oak (Quercus sp.) in Columbia, S.C. and was grown in medium CYG40 for 21 days at 25° C. The isolation and description of the species is as follows:

Isolation—Bark discs were obtained by use of a leather punch (⅜″) and a hammer. The punch was hammered through the bark until it enters the xylem. The punched material was surface sterilized by dipping the material in ethanol for 1 minute; sodium hypochlorite for 3–5 minutes and finally ethanol for an additional half minute. The sodium hypochlorite dip is made from Chlorox ® or similar product diluted 1:3. The punched bark disc was placed in 100 mm petri dishes and incubated on agar media at 20°–25° C. until growth was observed. Mycelium of the above mentioned organism emerged from internal bark tissue. Mycelium was transferred to slants of potato dextrose agar (DIFCO) to initiate an axenic culture. In culture, MF 5809 exhibits the following morphological features.

Xylaria sp. (MF 5809)

Colony on oatmeal agar (Difco) covering a 9 cm Petri dish after 15 d at 25° C. and 50% relative humidity in 12 hr photo period; growing edge appressed, margin indistinct, scalloped, roycellium at first white, velvety, followed by a distinct zone of velvety, olive-black, carbonaceous mycelium which is the color and texture at maturity, is aerial mycelium at colony center (inoculation point) white, cottony, sparse. Stromata few, restricted to colony center, robust, base villose, "mole" type, 1.0–1.5×0.4–0.6 cm, olive-black, apical portion white to tan, dissected. Teleomorph and anamorph absent. Carbonaceous hyphae thick-walled, bristle-like appearance, olivaceous, 6.0–7.0 gm wide. Hyphae from white, underlying mycelium, hyaline, thin-walled, smooth, 4.0–5.0 gm. Reverse uncolored. Exudate clear droplets on colony surface and stromata.

Because of the characteristic stromata and colony morphology, this endophytic fungus is easily placed in the genus Xylaria. The isolate produces no teleomorph (sexual state) or anamorph (asexual state) in culture. The characteristics present in MF 5809 do not fit into any of the species described in Callan, B. E. and J. D. Rogers. 1992. A synoptic key to Xylaria species from continental United States and Canada based on cultural and anamorphic features. Mycotaxon. 46: 141-154). Some individual key characters of this isolate, such as growth rate or stroma morphology, may be similar to those of different Xylaria species, but the panoply of characters do not fit any of the reported species.

Compound I may be obtained by cultivating MF5809, Xylaria sp., ATCC accession No. 74223 in a suitable nutrient medium under conditions hereinafter described until a substantial amount of the product is formed in the culture medium, harvesting by filtration and chromatographic separation of the active component from the fermentation medium, then concentrating the solution containing the active components, and subjecting the concentrated solution to a second chromatographic separation procedure to isolate Compound I.

Suitable nutrient medium contain sources of carbon and nitrogen assimilable by the microorganism and also containing low levels of inorganic salts. The medium may be supplemented with trace metals, although if complex sources of carbon and nitrogen are employed, trace metals are usually present in the complex sources.

Suitable sources of carbon include glycerol, sugars, sugar alcohols, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 40 percent by weight of the medium is satisfactory. These carbon sources can be used individually or several such carbon sources may be combined in the same medium.

The sources of nitrogen include amino acids such as glycine, arginine, threonine, methionine and the like, ammonium salt, as well as complex sources such as yeast hydrolysates, yeast autolysates, yeast cells, tomato paste, soybean meal, casein hydrolysates, yeast extracts, corn steep liquors, distillers solubles, cottonseed meal, meat extract, and the like. The various sources of nitrogen can be used alone or in combination in amounts ranging from 0.2 to 10 percent by weight of the medium.

Among the nutrient inorganic salts, which can be incorporated in the culture media are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

The cultivation generally is carded out first by growing the culture in a seed medium such as KF seed medium 3 days and then employing a portion of the cultivated seed medium to inoculate the production medium such as CYG40 production medium. The production cultures are then grown for up to 21 days, preferably 7 to 21 days.

The seed production media most frequently employed in cultivation are as follows:

TABLE 1

| Composition of KF Seed Medium | |
|---|---|
| | per liter of distilled H$_2$O |
| Corn Steep Liquor | 5 g |
| Tomato Paste | 40 g |
| Oat flour | 10 g |
| Glucose | 10 g |
| Trace Element Mix* | 10 ml |
| pH = 6.8 | |
| FeSO$_4$.7H$_2$O | 1 g |
| MnSO$_4$.4H$_2$O | 1 g |
| CuCl$_2$.2H$_2$O | 25 mg |
| CaCl$_2$ | 100 mg |
| H$_3$BO$_3$ | 56 mg |
| (NH$_4$)$_6$Mo$_7$O$_{24}$.4H$_2$O | 19 mg |
| ZnSO$_4$.7H$_2$O | 200 mg |

*Trace Element Mix

TABLE 2

| Composition of CYG40 Production Medium | |
|---|---|
| | per liter of distilled H$_2$O |
| Cornmeal (yellow) | 50 g |
| Yeast Extract | 1 g |
| Dextrose | 40 g |
| No pH adjustment | |

After completion of the fermentation period, in the preferred procedure, whole broth at near neutral pH (6.5) was filtered and passed through an anion exchange resin such DOWEX 1. Active compound was eluted with a suitable salt such as 2.5% NaCl, and the ICE-active NaCl fractions from the resin were pooled and passed through a reverse-phase resin such as SP 207 and eluted with water. The ICE-active fractions were lyophilized, reconstituted and filtered through a microporous filter.

Compound can be isolated further by purification using HPLC such as by passage through a C$_4$ radial compression column. An isocratic flow rate of 10 mL per minute of water is preferred for eluting the active compound. Compounds of the instant invention are conveniently prepared using the procedures described generally below and more explicitly described in the Example section thereafter.

This invention also relates to a method of treatment for patients (including man and/or mammalian animals raised in the dairy, meat, or fur industries or as pets) suffering from disorders or diseases which can be attributed to ICE as previously described, and more specifically, a method of treatment involving the administration of the ICE inhibitor of formula (I) as the active constituents.

Accordingly, disease states in which the ICE inhibitor of Formula I may be useful as therapeutic agents include, but are not limited to, infectious diseases where active infection exists at any body site, such as meningitis and salpingitis; complications of infections including septic shock, disseminated intravascular coagulation, and/or adult respiratory distress syndrome; acute or chronic inflammation due to antigen, antibody, and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis. Immune-based diseases which may be responsive to ICE inhibitors of Formula I include but are not limited to conditions involving T-cells and/or macrophages such as acute and delayed hypersensitivity, graft rejection, and graft-versus-host-disease; auto-immune diseases including Type I diabetes mellitus and multiple sclerosis. ICE inhibitors of Formula I may also be useful in the treatment of bone and cartilage resorption as well as diseases resulting in excessive deposition of extracellular matrix such as interstitial pulmonary fibrosis, cirrhosis, systemic sclerosis, and keloid formation. ICE inhibitors of Formula I may also be useful in treatment of certain tumors which produce IL 1 as an autocrine growth factor and in preventing the cachexia associated with certain tumors.

For the treatment the above mentioned diseases, the compounds of formula (I) may be administered orally, topically, parenterally, by inhalation spray or rectally in dosage unit formulations containing conventional nontoxic pharmaceutically acceptable carriers, adjuvants and vehicles. The term parenteral as used herein includes subcutaneous injections, intravenous, intramuscular, intracisternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, cornstarch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides; for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known an using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed. (For purposes of this application, topical application shall include mouth washes and gargles.)

Dosage levels of the order of from about 0.05 mg to about 140 mg per kilogram of body weight per day are useful in the treatment of the s above-indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to illustrate the preparation of compounds of Formula I, and as such are not intended to limit the invention as set forth in the claims appended, thereto.

EXAMPLE 1

Production of the ICE- active gamma-pyrone-3-acetic acid, by fermentation of fungus MF5809, Xylaria sp.

Organism MF5809 was isolated from a living bark of a live oak (Quercus sp.) in Columbia, S.C. and was initially grown in medium CYG40 (Table 2) for 21 days at 25 °C.

General Growth Conditions: MF5809 was grown in cotton-plugged, 250-ml Erlenmeyer flasks containing either 54 ml of the KF seed medium (Table 1 ) or 45 ml of CYG40 production medium (composition in Table 2). Cultures were incubated at 25° C. on a rotary shaker at 5-cm throw at 220 rpm for 3 days in seed medium or for up to 21 days in production medium.

Preparation of Standardized Frozen Inoculum: An initial source material of MF5809 was used to inoculate KF seed medium. The resulting 3-day culture was used to make frozen vegetative mycelia by mixing the broth with an equal volume of 20% glycerol and dispensing 2-ml portions of the mixture into sterile vials for storage at −80 ° C. A second set of frozen vegetative mycelia was made by the same procedure from a KF culture that had been inoculated with mycelia from the first set of vials.

Preparation of the Seed Culture: A flask of KF seed medium was inoculated with a 2-ml portion of frozen vegetative mycelia and incubated for 3 days.

Production Protocol: A 2-ml aliquot of the seed culture was used to inoculate each 45-ml portion of CYG40 production medium. These production cultures were grown at for up to 21 days in 250 ml flasks. A study of the course of production showed that production of the active compound began by day 7 and that activity remained at day 21.

Harvest: After 10-21 days, the contents of the flasks were pooled for isolation of gamma-pyrone-3-acetic acid.

EXAMPLE 2

Isolation of formula I from fermentation Broth

Whole broth at pH 6.5 (300 mL) was filtered through a glass Buchner funnel (fine porosity) yielding 250 mL. Filtered broth was passed through 50 mL DOWEX 1 (1×2) anion exchange resin. Active compound was eluted with one column volume of 2.5% NaCl. The ICE-active NaCl fractions from the DOWEX 1 resin were pooled and passed through 50 mL of the MITSUI-SHI reverse-phase resin SP 207 and eluted with water.

The ICE-active fractions eluted between 0.5 and 2.0 column volumes. The ICE-active fractions were pooled and lyophilized for 24 hours. The lyophilized fractions were reconstituted with 10 mL of water and filtered through a 0.20μ filter.

Compound was isolated further by purification using HPLC. Two mL of filtered solution was passed through a C4 radial compression column (25×100 mm, WATERS ASSOCIATES) and an isocratic flow rate of 10 mL per minute of water was used to elute the active compound. A total of 5 runs were performed with fractions being collected at one minute intervals. The fractions were tested for ICE-activity. The active fractions eluted between 9-10 minutes. The ICE-active-rich cuts from each run were pooled and lyophilized. The resulting material appeared to be an oily brown substance that was soluble in water, methanol, and DMSO. Estimates of 7 mg of compound can be isolated from 300 ml of whole broth.

The molecular formula $C_7H_6O_4$ was determined by high resolution EI-MS (calc. 154.0266; found 154.0268).

$^{13}C$ NMR ($D_2O$, 125 MHz) 34.6, 116.4, 126.6, 157.0, 158.9, 179.1, 182.1 ppm referenced to internal dioxane at 67.4 ppm downfield of TMS.

$^1H$ NMR ($D_2O$, 500 MHz) δ3.02 (d, j=1,2H), 6.28 (d, j=5.5, 1H), 7.86 (dt, j=1.0, 1.0, 1H), 7.89 (dd, j=1.0, 5.5, 1H), referenced to internal dioxane at δ3.53 downfield of TMS.

EXAMPLE 3

Assay for assessing the ICE activity of compound of Formula I

Gamma-pyrone-3-acetic acid was assessed for ICE activity by the procedure of Thomberry, et al (1992) Nature Vol. 356 pp 768-774. The compound was found to possess an $IC_{50}$ of 0.2 μg/ml at pH 6.5 and 1 mM DDT; and an $IC_{50}$ of 0.7 ∞g/ml at pH 7:5 and 1 mM DDT.

What is claimed is:

1. A pharmaceutical composition for inhibiting ICE comprising a pharmaceutically acceptable carrier and a non-toxic therapeutically effective amount of compound of formula I which is gamma-pyrone-3-acetic acid

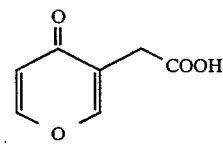

or a pharmaceutically acceptable salt thereof wherein said effective amount is 5 mg to 500 mg of formula I.

2. A method of treating inflammation in a patient in need of such treatment comprising: administration to a patient in need of such treatment of a non-toxic therapeutically effective amount of gamma-pyrone-3-acetic acid.

3. A method according to claim 2 wherein said inflammation is due to septic shock.

4. A method according to claim 2 wherein said inflammation is due to arthritis.

* * * * *